(12) United States Patent
Ohuchi et al.

(10) Patent No.: US 10,278,670 B2
(45) Date of Patent: May 7, 2019

(54) ULTRASOUND DIAGNOSTIC APPARATUS AND METHOD OF CONTROLLING ULTRASOUND DIAGNOSTIC APPARATUS

(71) Applicant: Toshiba Medical Systems Corporation, Otawara-shi (JP)

(72) Inventors: Hiroyuki Ohuchi, Otawara (JP); Tetsuya Yoshida, Bergschenhoek (NL); Tetsuya Kawagishi, Nasushiobara (JP); Yoko Okamura, Irvine, CA (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 660 days.

(21) Appl. No.: 14/694,391

(22) Filed: Apr. 23, 2015

(65) Prior Publication Data
US 2015/0223776 A1    Aug. 13, 2015

Related U.S. Application Data

(63) Continuation of application No. PCT/JP2013/078740, filed on Oct. 23, 2013.

(30) Foreign Application Priority Data

Oct. 23, 2012 (JP) ................................ 2012-234086

(51) Int. Cl.
*A61B 17/34*  (2006.01)
*A61B 8/08*  (2006.01)
(Continued)

(52) U.S. Cl.
CPC .............. *A61B 8/0841* (2013.01); *A61B 8/14* (2013.01); *A61B 8/461* (2013.01); *A61B 8/463* (2013.01);
(Continued)

(58) Field of Classification Search
None
See application file for complete search history.

(56) References Cited

U.S. PATENT DOCUMENTS 9,610,094 B2* 4/2017 Yoshida ................... A61B 8/06
9,833,216 B2* 12/2017 Ohuchi ............... A61B 8/0841
(Continued)

FOREIGN PATENT DOCUMENTS

CN    101797167 A    8/2010
JP    2006-150069 A   6/2006
(Continued)

OTHER PUBLICATIONS

International Search Report dated Nov. 26, 2013 for PCT/JP2013/078740 filed on Oct. 23, 2013 with English Translation.
(Continued)

*Primary Examiner* — Angela M Hoffa
(74) *Attorney, Agent, or Firm* — Oblon, McClelland, Maier & Neustadt, L.L.P.

(57) ABSTRACT

In general, according to one embodiment, an ultrasonic diagnostic apparatus is used to observe a position and puncture direction of a puncture needle in an object in a paracentesis, and comprises data acquisition unit, image generation unit and a display. The data acquisition unit acquires a plurality of first ultrasound data concerning an inside of the object, acquire a plurality of second ultrasound data concerning the inside of the object, and acquire a plurality of third ultrasound data concerning the inside of the object. The image generation unit generates a tissue image displaying a living body tissue by using the first ultrasound data, generate a puncture image displaying the puncture needle based on image processing using the second ultrasound data and the third ultrasound data, and generate a composite image visualizing the living body tissue and the (Continued)

puncture needle by using the tissue image and the puncture image.

12 Claims, 14 Drawing Sheets

(51) Int. Cl.
  *A61B 8/00* (2006.01)
  *A61B 8/14* (2006.01)
(52) U.S. Cl.
  CPC .......... *A61B 8/5207* (2013.01); *A61B 8/5246* (2013.01); *A61B 2017/3413* (2013.01)

(56) References Cited

U.S. PATENT DOCUMENTS

| | | | | |
|---|---|---|---|---|
| 2002/0173719 A1* | 11/2002 | Zhao | ..................... | A61B 8/0833 600/437 |
| 2004/0002653 A1* | 1/2004 | Greppi | ..................... | A61B 8/06 600/439 |
| 2004/0133106 A1* | 7/2004 | Kakee | ..................... | A61B 8/481 600/437 |
| 2010/0204579 A1* | 8/2010 | Yoshida | ............... | A61B 8/0833 600/443 |
| 2011/0249878 A1* | 10/2011 | Pagoulatos | .......... | A61B 8/0841 382/131 |
| 2012/0253181 A1* | 10/2012 | Okamura | ............. | A61B 8/0841 600/424 |

FOREIGN PATENT DOCUMENTS

| | | |
|---|---|---|
| JP | 2008-12150 A | 1/2008 |
| JP | 2008-178470 A | 8/2008 |
| JP | 2010-183935 A | 8/2010 |
| JP | 2012-213606 A | 11/2012 |
| WO | WO 2011/127191 A1 | 10/2011 |

OTHER PUBLICATIONS

Written Opinion dated Nov. 26, 2013 for PCT/JP2013/078740 filed on Oct. 23, 2013.
Japanese Office Action dated Jul. 25, 2017 in Patent Application No. 2013-220667 (without English Translation).
Combined Office Action and Search Report dated May 14, 2015 in Chinese Patent Application No. 201380003446.3 (with English translation of categories of cited documents).

* cited by examiner

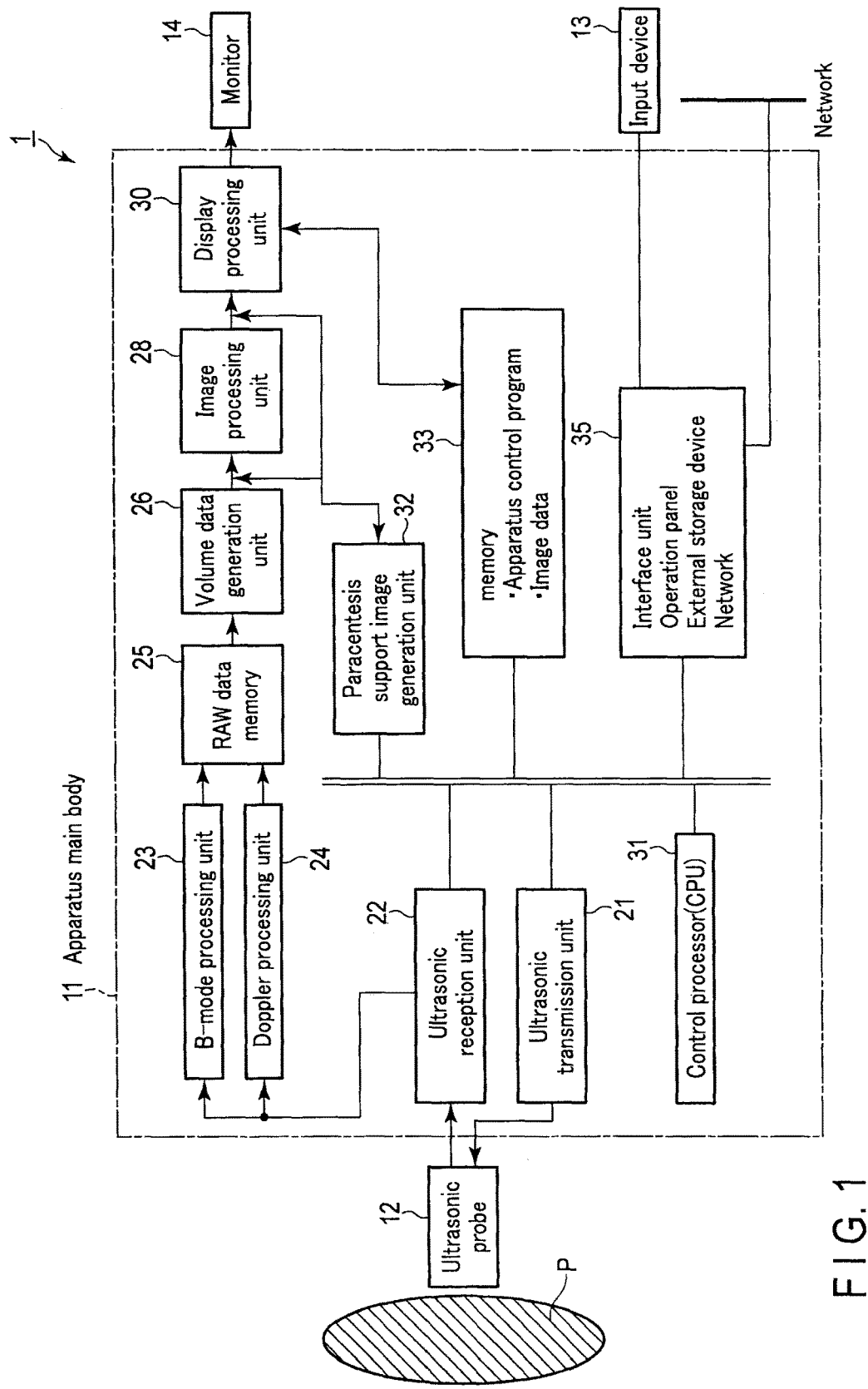
F I G. 1

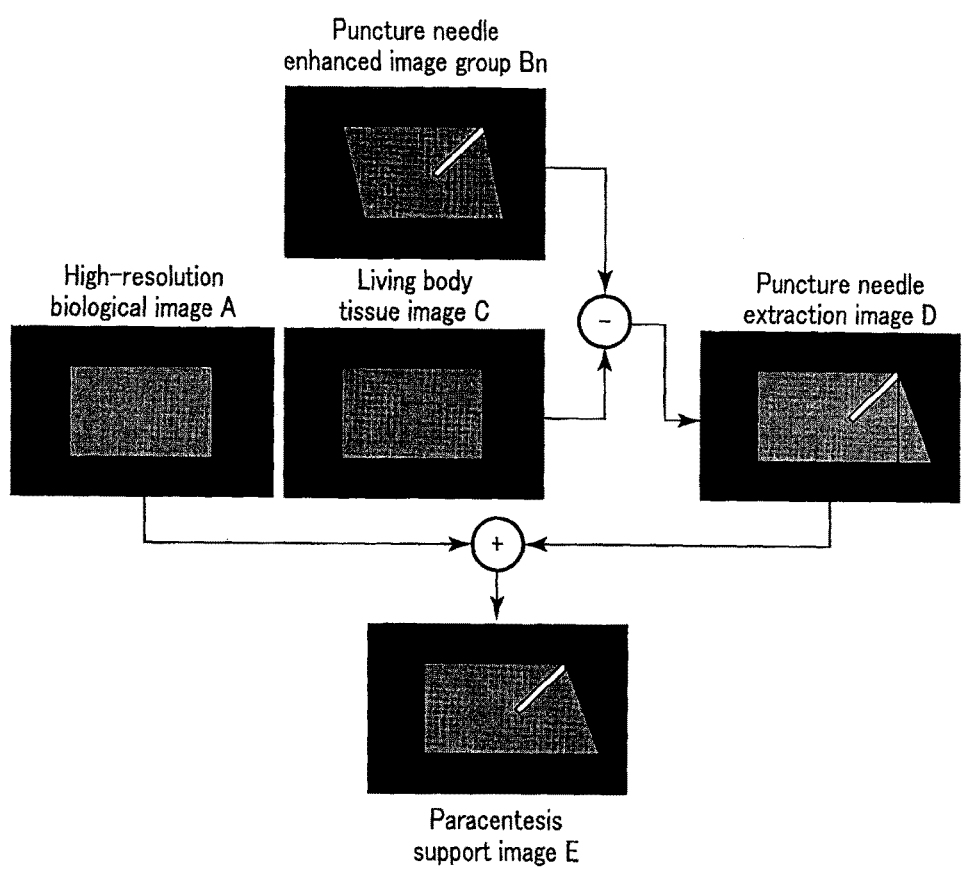
F I G. 10

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation Application of PCT Application No. PCT/JP2013/078740, filed Oct. 23, 2013 and based upon and claiming the benefit of priority from Japanese Patent Application No. 2012-234086, filed Oct. 23, 2012 the entire contents of all of which are incorporated herein by reference.

FIELD

Embodiments described herein relate to an ultrasound diagnostic apparatus for improving the visibility of a needle without degrading the quality of a biological image in puncturing under ultrasound guidance, in particular, and a method of controlling the ultrasound diagnostic apparatus.

BACKGROUND

Ultrasound diagnosis enables to display in real time how the heart beats or the fetus moves, by simply bringing an ultrasound probe into contact with the body surface. This technique is highly safe, and hence allows repeated examination. Furthermore, this system is smaller in size than other diagnostic apparatuses such as X-ray, CT, and MRI apparatuses and can be moved to the bedside to be easily and conveniently used for examination. In addition, ultrasound diagnosis is free from the influences of exposure using X-rays and the like, and hence can be used in obstetric treatment, treatment at home, and the like.

In addition, an ultrasound diagnostic apparatus is used not only for image diagnosis but also for an RFA (Radio Frequency Ablation) as a local treatment method for hepatocellular cancers, a biopsy which examines hepatocellular tissues, and the like. In such a treatment or examination, in order to accurately make a puncture in a region of interest by using a puncture needle, an ultrasound diagnostic apparatus is used to monitor the region of interest and the puncture needle in real time.

When, however, using a conventional ultrasound diagnostic apparatus for monitoring in a paracentesis, the following inconveniences occur.

First of all, when performing a paracentesis while monitoring a general ultrasound image provided by the conventional ultrasound diagnostic apparatus, the operator sometimes faces difficulty in seeing the needle due to the influence of the position of a lesion or the insertion angle of the needle. Under the current situation, the solution of such a problem largely depends on doctor's experience and knowledge. For example, the doctor indirectly grasps the position or the like of the needle while seeing the movement of the tissue when moving the needle.

In addition, as shown in, for example, FIG. 14, there is available a technique of performing ultrasound image monitoring in a paracentesis by generating an image C of a needle extracted by subtracting an image A obtained by oblique scanning (scanning with a beam angle being adjusted to make an ultrasound beam vertically strike the needle) from an image B obtained by general ultrasound scanning (without performing oblique scanning), and using the image obtained by adding the image A to the image C. In the use of this technique, however, when executing the above oblique scanning, grating lobes may occur depending on the beam shape and the like. This may lead to the generation of artifacts in an image. In addition, assume that oblique scanning is performed such that an ultrasound beam vertically strikes the needle. In this case as well, even a slight shift of the position of the needle from a scan slice may fail to preferably visualize the needle.

In consideration of the above situation, it is an object to provide an ultrasound diagnostic apparatus which can monitor a living body tissue and a puncture needle with a favorable high-quality image when performing a paracentesis, and a method of controlling the ultrasound diagnostic apparatus.

BRIEF DESCRIPTION OF THE DRAWINGS

FIG. 1 is a block diagram showing the arrangement of an ultrasound diagnostic apparatus 1 according to an embodiment.

FIG. 10 is a view for explaining the effects of an ultrasound diagnostic apparatus according to this embodiment.

DETAILED DESCRIPTION

Figure 2:
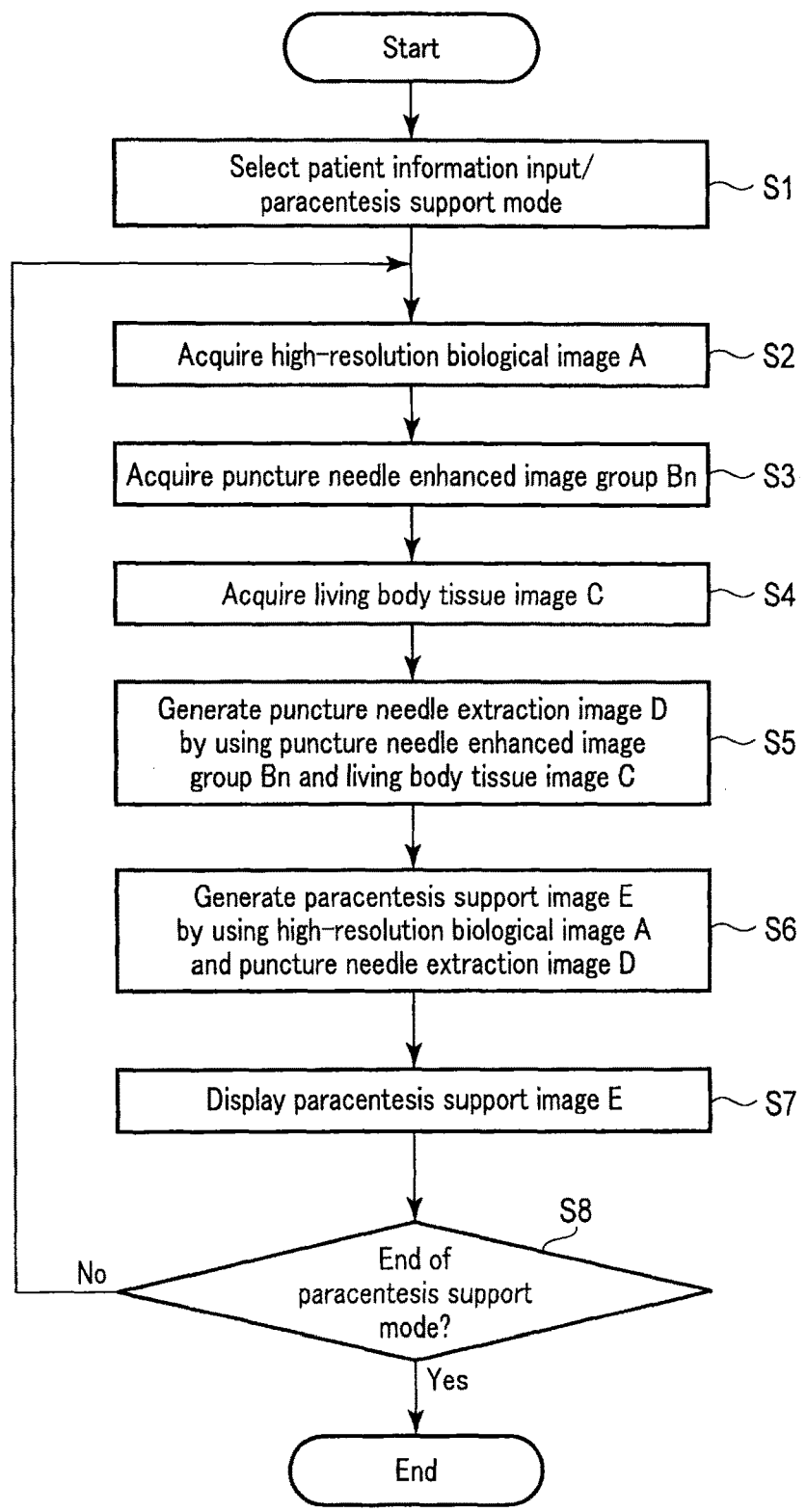
FIG. 2 is a flowchart showing a procedure for processing (paracentesis support processing) based on a paracentesis support function.

An ultrasonic diagnostic apparatus disclosed by this embodiment is used to observe a position and puncture direction of a puncture needle in an object in a paracentesis, and comprises; data acquisition unit configured to acquire a plurality of first ultrasound data by executing a first ultrasound scan under a first transmission/reception setting concerning an inside of the object, acquire a plurality of second ultrasound data by executing a second ultrasound scan under a second transmission/reception setting concerning the inside of the object, and acquire a plurality of third ultrasound data by executing a third ultrasound scan under a third transmission/reception setting concerning the inside of the object; and image generation unit configured to generate a tissue image displaying a living body tissue by using the first ultrasound data, generate a puncture image displaying the puncture needle based on image processing using the second ultrasound data and the third ultrasound data, and generate a composite image visualizing the living body tissue and the puncture needle by using the tissue image and the puncture image; and a display configured to display the composite image.

Embodiments will be described below with reference to the accompanying drawings. Note that the same reference numerals in the following description denote constituent elements having almost the same functions and arrangements, and a repetitive description will be made only when required.

FIG. 1 is a block diagram showing the arrangement of an ultrasound diagnostic apparatus 1 according to an embodiment. As shown in FIG. 1, the ultrasound diagnostic apparatus 1 includes an ultrasound probe 12, an input device 13, a monitor 14, ultrasound transmission unit 21, ultrasound reception unit 22, B-mode processing unit 23, Doppler processing unit 24, a RAW data memory 25, volume data generation unit 26, an image processing unit 28, a display processing unit 30, a control processor (CPU) 31, a paracentesis support image generation unit 32, a storage unit (memory) 33, and an interface 35. The function of each constituent element will be described below.

The ultrasound probe 12 is a device (probe) which transmits ultrasound waves to an object, and receives reflected waves from the object based on the transmitted ultrasound waves. The ultrasound probe 12 has, on its distal end, an array of a plurality of piezoelectric transducers, a matching layer, a backing member, and the like. The piezoelectric transducers transmit ultrasound waves in a desired direction in a scan region based on driving signals from the ultrasound transmission unit 21, and convert reflected waves from the object into electrical signals. The matching layer is an intermediate layer which is provided for the piezoelectric transducers to make ultrasound energy efficiently propagate. The backing member prevents ultrasound waves from propagating backward from the piezoelectric transducers. When the ultrasound probe 12 transmits an ultrasound wave to an object P, the transmitted ultrasound wave is sequentially reflected by a discontinuity surface of acoustic impedance of internal body tissue, and is received as an echo signal by the ultrasound probe 12. The amplitude of this echo signal depends on an acoustic impedance difference on the discontinuity surface by which the echo signal is reflected. The echo produced when a transmitted ultrasound pulse is reflected by a moving blood flow is subjected to a frequency shift depending on the velocity component of the moving body in the ultrasound transmission/reception direction by the Doppler effect. Note that this embodiment will exemplify a case in which one-dimensional ultrasound probe having ultrasound transducers arrayed in a predetermined direction is used as the ultrasound probe 12.

The input device 13 is connected to an apparatus main body 11 and includes various types of switches, buttons, a trackball, a mouse, and a keyboard which are used to input, to the apparatus main body 11, various types of instructions, conditions, an instruction to set a region of interest (ROI), various types of image quality condition setting instructions, and the like from an operator. The input device 13 also includes a dedicated switch for inputting a diagnostic region, a dedicated knob for controlling a color data range used for visualization, and a dedicated knob for controlling the degree of transparency (opacity) of voxels, used in a near-lumen blood flow extraction function (to be described later).

The monitor 14 displays morphological information and blood flow information in the living body as images based on video signals from the display processing unit 30.

The ultrasound transmission unit 21 includes a trigger generation circuit, delay circuit, and pulser circuit (none of which are shown). The trigger generation circuit repeatedly generates trigger pulses for the formation of transmission ultrasound waves at a predetermined rate frequency fr Hz (period: 1/fr sec). The delay circuit gives each trigger pulse a delay time necessary to focus an ultrasound wave into a beam and determine transmission directivity for each channel. The pulser circuit applies a driving pulse to the probe 12 at the timing based on this trigger pulse.

The ultrasound reception unit 22 includes an amplifier circuit, A/D converter, delay circuit, and adder (none of which are shown). The amplifier circuit amplifies an echo signal received via the probe 12 for each channel. The A/D converter converts each amplified analog echo signal into a digital echo signal. The delay circuit gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasound transmission/reception in accordance with reception directivity and transmission directivity.

The B-mode processing unit 23 receives an echo signal from the reception unit 22, and performs logarithmic amplification, envelope detection processing, and the like for the signal to generate data whose signal intensity is expressed by a luminance level.

The Doppler processing unit 24 extracts a blood flow signal from the echo signal received from the ultrasound reception unit 22, and generates blood flow data. In general, the Doppler processing unit 24 extracts a blood flow by CFM (Color Flow Mapping). In this case, the Doppler processing unit 24 analyzes the blood flow signal to obtain blood flow information such as mean velocities, variances, and powers as blood flow data at multiple points.

The raw data memory 25 generates B-mode raw data as B-mode data on three-dimensional ultrasound scanning lines by using a plurality of B-mode data received from the B-mode processing unit 23. The raw data memory 25 also generates blood flow raw data as blood flow data on three-dimensional ultrasound scanning lines by using a plurality of blood flow data received from the Doppler processing unit 24. Note that for the purpose of reducing noise or smooth concatenation of images, a three-dimensional filter may be inserted after the raw data memory 25 to perform spatial smoothing.

The volume data generation unit 26 generates B-mode volume data or blood flow volume data from the B-mode RAW data received from the RAW data memory 25 by executing RAW/voxel conversion.

The image processing unit 28 performs predetermined image processing such as volume rendering, MPR (Multi Planar Reconstruction), and MIP (Maximum Intensity Projection) for the volume data received from the volume data generation unit 26. Note that for the purpose of reducing noise or smooth concatenation of images, a two-dimensional filter may be inserted after the image processing unit 28 to perform spatial smoothing.

The display processing unit 30 executes various types of processing associated with a dynamic range, luminance (brightness), contrast, γ curve correction, RGB conversion, and the like for various types of image data generated/ processed by the image processing unit 28.

The control processor 31 has the function of an information processing apparatus (computer) and controls the operation of the main body of this ultrasound diagnostic apparatus. The control processor 31 reads out a dedicated program for implementing the paracentesis support function (to be described later) from the storage unit 33, and expands the program in its own memory, and executes computation, control, and the like associated with each type of processing.

The paracentesis support image generation unit 32 generates an image for supporting a paracentesis based on the paracentesis support function (to be described later).

The storage unit 33 stores a dedicated program for implementing the paracentesis support function (to be described later), diagnosis information (patient ID, findings by doctors, and the like), a diagnostic protocol, transmission/reception conditions, a program for implementing a speckle removal function, a body mark generation program, and a conversion table in which a color data range used for visualization is set for each diagnostic region in advance, and other data groups. The storage unit 33 is also used to store images in the image memory (not shown), as needed. It is possible to transfer data in the storage unit 33 to an external peripheral device via the interface 35.

The interface 35 is an interface associated with the input device 13, a network, and a new external storage device (not shown). The interface 32 can transfer, via a network, data such as ultrasound images, analysis results, and the like obtained by this apparatus to another apparatus.

(Paracentesis Support Function)

The paracentesis support function of the ultrasound diagnostic apparatus 1 will be described next. This function generates and presents a paracentesis support image, with a living body tissue and a puncture needle being always favorably visualized, while setting a region to be scanned with ultrasound waves so as to prevent the region from coming off the puncture needle, when the operator performs a paracentesis while monitoring the living body tissue and the puncture needle by using the ultrasound diagnostic apparatus.

FIG. 2 is a flowchart showing a procedure for processing (paracentesis support processing) based on this paracentesis support function. The contents of processing executed in each step in the flowchart will be described.

[Input of Patient Information and the Like and Selection of Paracentesis Support Mode: Step S1]

The operator inputs patient information, examination information, and the like and selects the paracentesis support mode of executing the paracentesis support function via the operation unit 33 (step S1). A storage device 29 automatically stores the input and selected various types of information. In addition, the CPU 31 activates a program for executing the paracentesis support function in response to the selecting operation for the paracentesis support mode.

[Acquisition of High-Resolution Biological Image A: Step S2]

The apparatus then executes an imaging method of favorably drawing a living body tissue, e.g., tissue harmonic imaging, and executes ultrasound transmission/reception under transmission/reception settings, thereby acquiring the high-resolution biological image A with the living body tissue being visualized with a high resolution (step S2). Note that the high-resolution biological image A is not limited to an image captured by tissue harmonic imaging and may be an image captured by using a reception signal containing a fundamental component in a frequency band. The apparatus may further generate the high-resolution biological image A by executing at least one of addition processing, subtraction processing, maximum value projection processing, minimum value projection processing, and averaging processing using ultrasound data over a plurality of frames (a plurality of volumes). Likewise, the ultrasound image over a plurality of frames (a plurality of volumes) may be an image captured by tissue harmonic imaging or an image captured with a fundamental wave component falling in a frequency band.

In addition, as a capturing technique of tissue harmonic imaging, a pulse subtraction method (a technique of obtaining reception data in a harmonic band by adding a plurality of pulses which differ in polarity and phase) may be used. In this case, the number of pulses to be added is not specifically limited, and an arbitrary number of pulses may be used.

Furthermore, the apparatus may generate the high-resolution biological image A by acquiring ultrasound data over a plurality of frames (a plurality of volumes) by executing a pulse subtraction method, and executing addition processing and subtraction processing using the data.

[Acquisition of Puncture Needle Enhanced Image B: Step S3]

The apparatus then acquires the puncture needle enhanced image B by executing oblique scanning with transmission/reception directions being substantially perpendicular to the longitudinal direction of a needle, while suppressing grating lobes as much as possible at the time of transmission and the time of reception by, for example, using a transmission waveform with a relatively low frequency and using the fundamental wave component, of reception signals, which corresponds to the frequency of the transmission waveform for visualization (step S3).

Note that transmission/reception settings are not limited to the above contents. For example, the apparatus can control transmission/reception conditions by using at least one of the element pitch of the ultrasound transducers of the ultrasound probe 12 to be used, the transmission/reception frequency characteristics of the ultrasound transducers, an oblique angle, and the like. It is theoretically known, in particular, that it is possible to prevent the appearance of grating lobes by satisfying the following inequality:

$$d<\lambda/(1+\sin\theta_M) \qquad (1)$$

where d, λ, and $\theta_M$ are respectively an element pitch [mm], a wavelength [mm], and the scanning angle (oblique angle or azimuth angle) [rad.] of a main lobe. In step S3, the CPU 31 automatically or the operator sets the wavelength (or frequency) of a transmission waveform, a reception center frequency, and a reception frequency band by the manual input from the input device 13 so as to satisfy inequality (1). In some case, however, there is no transmission/reception conditions satisfying inequality (1). In such a case, it is preferable to select conditions with reference to inequality (1) so as to prevent grating lobes from appearing in an image as much as possible.

It is preferable to set an oblique angle so as to transmit an ultrasound beam to the puncture needle at a vertical angle or a nearly vertical angle. When using a puncture adapter, it is possible to display a guideline for the puncture needle on an ultrasound image by registering the angle of the puncture needle with reference to the adapter in the ultrasound diagnostic apparatus. In such a case, the CPU 31 automatically decides an oblique angle based on the registered angle of the puncture needle. When detecting the position and direction of the puncture needle by using a position sensor, the CPU 31 automatically decides an oblique angle based on the position or the like detected by the position sensor. Even when not registering a puncture needle angle using a puncture adapter or not using any position sensor, the CPU 31 may automatically decide an oblique angle with reference to the direction of the puncture needle by detecting the puncture needle on an ultrasound image by using, for example, a general edge detection technique or line segment detection technique. In addition, the CPU 31 may set and adjust an oblique angle in accordance with a manual input from the input device 13 with reference to the direction of the puncture needle on an ultrasound image.

[Acquisition of Living Body Tissue Image C: Step S4]

The apparatus then generates the living body tissue image C by executing ultrasound transmission/reception under substantially the same transmission/reception conditions as those set at time of the acquisition of the puncture needle enhanced image B (i.e., the transmission/reception conditions set in step S3) except for a scanning angle upon setting the scanning angle of a main lobe to 0° (step S4).

Note that it is possible to change the execution order of steps S3 and S4 as needed. In addition, an ultrasound scanning region in step S3 need not be the same as that in step S4. That is, an ultrasound scanning region may only be set in step S3 to meet the purpose of visualizing the puncture needle while enhancing it. On the other hand, an ultrasound scanning region may only be set in step S4 so as to meet the purpose of canceling the tissue included in the puncture needle enhanced image B (for example, so as to include at least the tissue region included in the puncture needle enhanced image B).

[Generation of Puncture Needle Extraction Image D by Using Images B and C: Step S5]

The paracentesis support image generation unit 32 then generates the puncture needle extraction image D by image processing using the puncture needle enhanced image B and the living body tissue image C (step S5). For example, the paracentesis support image generation unit 32 compares the luminance values of the puncture needle enhanced image B with the luminance values of the living body tissue image C at the respective spatially corresponding positions. The paracentesis support image generation unit 32 generates the puncture needle extraction image D by assigning 0 for each position when the luminance value of the living body tissue image C is larger, and setting the luminance value of the puncture needle enhanced image B for each position when the luminance value of the puncture needle enhanced image B is larger. This will assign the luminance value of the puncture needle included in the puncture needle enhanced image B to a position corresponding to the puncture needle on the puncture needle extraction image D, and assigning a luminance value of 0 to a region outside the puncture needle on the puncture needle extraction image D. Therefore, the puncture needle extraction image D becomes an image obtained by extracting the puncture needle and favorably visualizing it.

Note that the method of generating the puncture needle extraction image D is not limited to the above method using the comparison between luminance values. For example, the apparatus may generate the puncture needle extraction image D by averaging or performing addition/subtraction processing (addition processing and subtraction processing) or the like for the luminance values of the puncture needle enhanced image B and the luminance values of the living body tissue image C for the respective spatially corresponding positions, and assigning the obtained values as luminance values at the respective positions.

In addition, the apparatus may adjust at least one of the gain or dynamic range of at least one of the puncture needle enhanced image B and the living body tissue image C so as to, for example, enhance (or suppress) the puncture needle or living body tissue, before the generation of the puncture needle extraction image D. There is a large difference in acoustic impedance between a hard material such as a puncture needle and a living body tissue. For this reason, a reflection signal from the puncture needle becomes much larger than a reflection signal from the living body tissue, and the puncture needle is displayed with a high luminance as compared with the surrounding living body tissue in the puncture needle enhanced image B. It is therefore possible to set the luminance of a position corresponding to a living body tissue to 0 when generating the puncture needle extraction image D by, for example, making the gain of the puncture needle enhanced image B lower that that of the living body tissue image C or making the tissue of the puncture needle enhanced image B have almost the same brightness as that of the tissue of the living body tissue image C. As a consequence, the apparatus can effectively extract the puncture needle corresponding to a high-luminance region when generating the puncture needle extraction image D.

[Generation/Display of Paracentesis Support Image E by Using High-Resolution Biological Image A and Puncture Needle Extraction Image D: Steps S6 and S7]

The paracentesis support image generation unit 32 then generates the paracentesis support image E by using the puncture needle extraction image D favorably visualizing the puncture needle and the high-resolution biological image A visualizing the living body tissue with a high resolution (step S6). More specifically, the paracentesis support image generation unit 32 compares the luminance values of the high-resolution biological image A visualizing only the living body with a high resolution with the luminance values of the puncture needle extraction image D with the puncture needle being extracted at the respective spatially corresponding positions, and assigns a large luminance value at each position, thereby generating the paracentesis support image E. This generates the paracentesis support image E which superimposes and displays the high-resolution needle image on the high-resolution biological image A with favorable image quality. Alternatively, the apparatus may generate the paracentesis support image E by executing at least one of addition processing, subtraction processing, maximum value projection processing, minimum projection processing, and averaging processing using the puncture needle extraction image D and the high-resolution biological image A.

A method of generating the paracentesis support image E is not limited to the above method using the comparison of luminance values. For example, the apparatus may generate the paracentesis support image E by executing averaging, addition/subtraction processing, or the like for the luminance values of the puncture needle extraction image D and the luminance values of the high-resolution biological image A at the respective spatially corresponding positions, and assigning the obtained values as luminance values at the respective positions. In addition, the apparatus may adjust at least one of the gain or dynamic range of at least one of the puncture needle extraction image D and the high-resolution biological image A before the generation of the paracentesis support image E. For example, the puncture needle extraction image D preferably displays only the high-luminance needle. In practice, however, a more than a little living body tissue image remains in the puncture needle extraction image D generated in step S5. In such a case, it is possible to display a region corresponding to the puncture needle with a high luminance by, for example, suppressing or eliminating a signal from the tissue region by narrowing the dynamic range of the puncture needle extraction image D, and increasing the gain. Note that it is possible to perform such gain and dynamic range adjustment automatically by generating a histogram concerning the luminance values of the puncture needle extraction image D and performing threshold processing using the generated histogram or manually by a manual operation with the input device 13.

[Repeated Generation/Display of Paracentesis Support Image during Paracentesis: Step S8]

The apparatus sequentially and repeatedly executes the above processing in steps S2 to S7 during a paracentesis.

Figure 3:
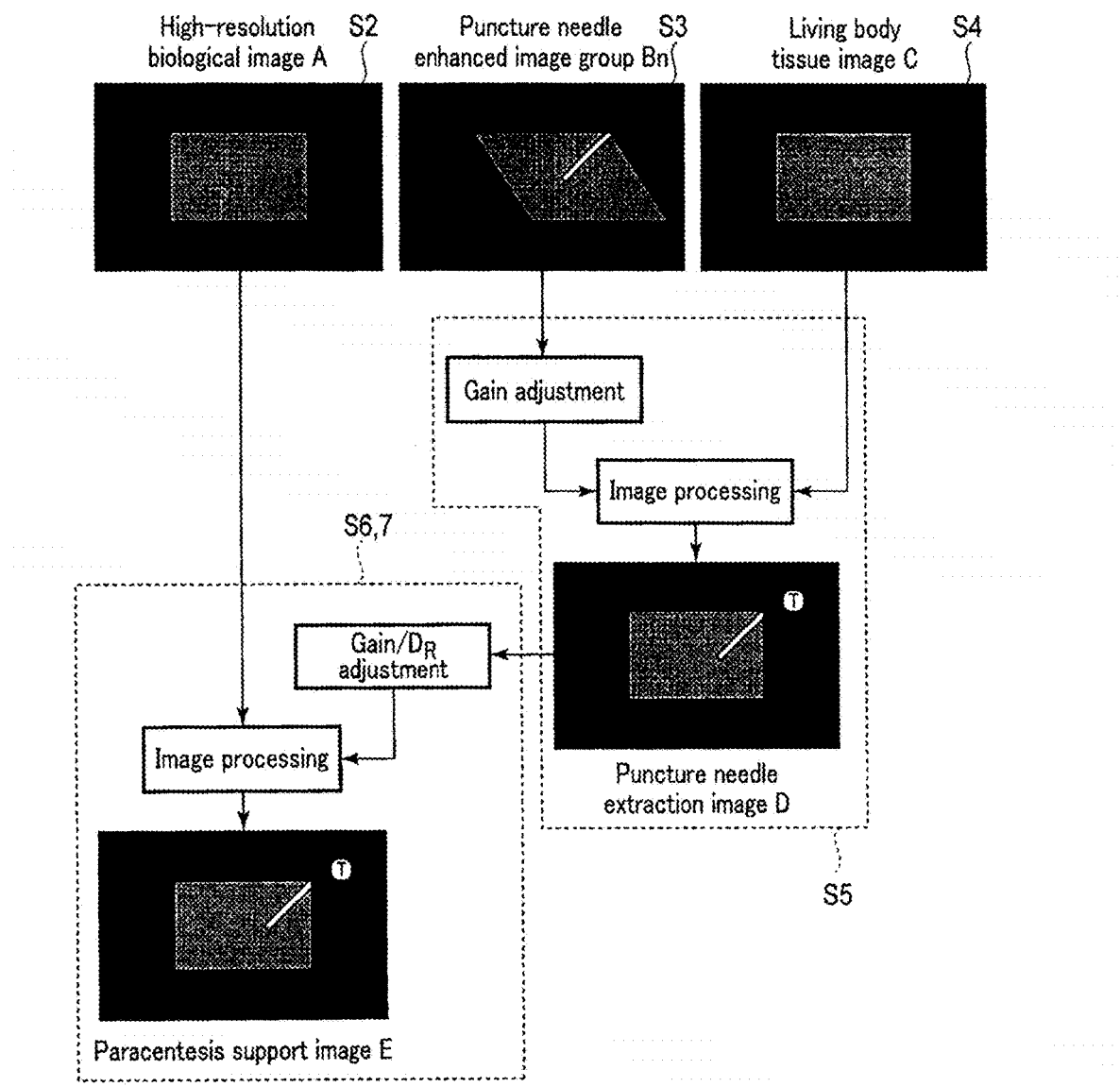
FIG. 3 is a view conceptually showing processing in steps S2 to S7 in FIG. 2.

FIG. 3 is a view conceptually showing the processing in steps S2 to S7 in FIG. 2. As shown in FIG. 3, the apparatus executes the processing corresponding to each of steps S2 to S7 to sequentially update the paracentesis support image E to the newest one and display it. The operator can easily visually check the relative positional relationship between the living body tissue and the puncture needle by observing the paracentesis support image E displayed in real time.

(First Modification)

Figure 4:
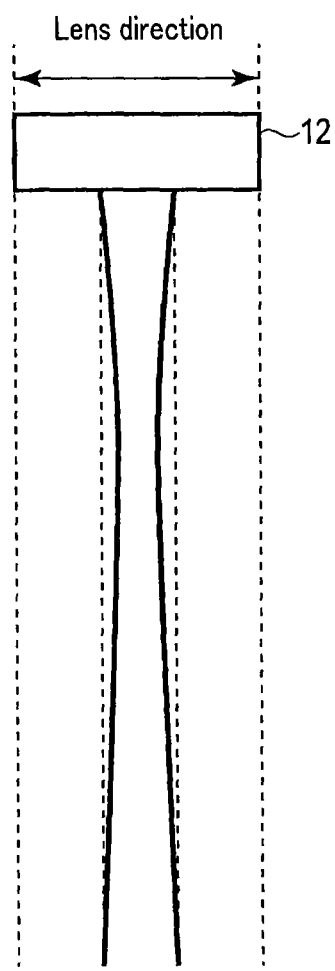
FIG. 4 is a view showing an example of a beam width in the lens direction when using a one-dimensional array probe.
Figure 5:
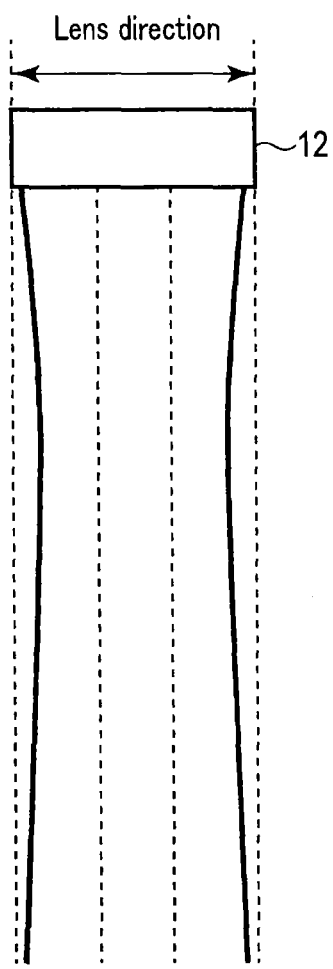
FIG. 5 is a view showing an example of a beam width in the lens direction when using a two-dimensional array probe.

The above embodiment has exemplified the case in which the ultrasound probe 12 is a one-dimensional array probe. However, the apparatus may use a one-and-half-dimensional array probe or two-dimensional array probe as the ultrasound probe 12. This makes it possible to capture a puncture needle enhanced image group Bn and the living body tissue image C upon increasing the beam width (see FIG. 5) in the lens direction (slice direction) when using the two-dimensional array probe as compared with the beam width (see FIG. 4) in the lens direction when using the one-dimensional array probe. As a consequence, it is possible to always favorably visualize the puncture needle even if the position of the puncture needle slightly shifts from a position immediately below the ultrasound probe 12.

Note that considering the purpose of visualizing the puncture needle, it seems that there is no need to increase the beam width in the lens direction when capturing the living body tissue image C. However, a large living body tissue remains in the puncture needle extraction image D when it is generated unless the spatial resolution of the living body tissue region of the puncture needle enhanced image group Bn is equal as much as possible to that of the living body tissue image C. In consideration of the above, when the beam width in the lens direction is increased when capturing the puncture needle enhanced image group Bn, it is preferable to also increase the beam width in the lens direction when capturing the living body tissue image C (equalizing the beam width with that when capturing the puncture needle enhanced image group Bn).

(Second Modification)

Figure 6:
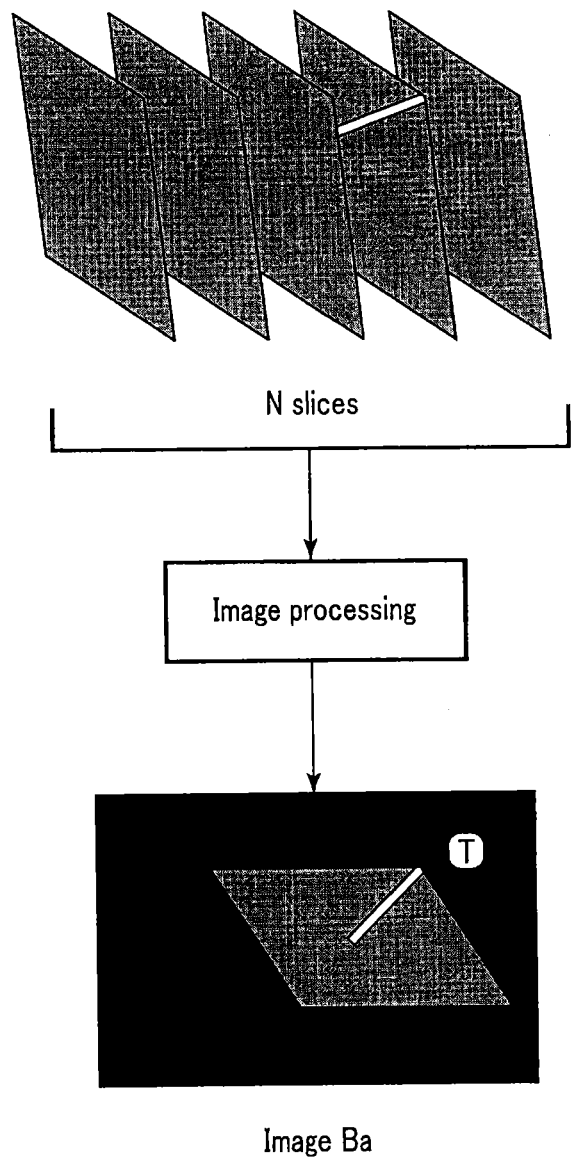
FIG. 6 is a view for explaining processing in step S3 according to the second modification.
Figure 7:
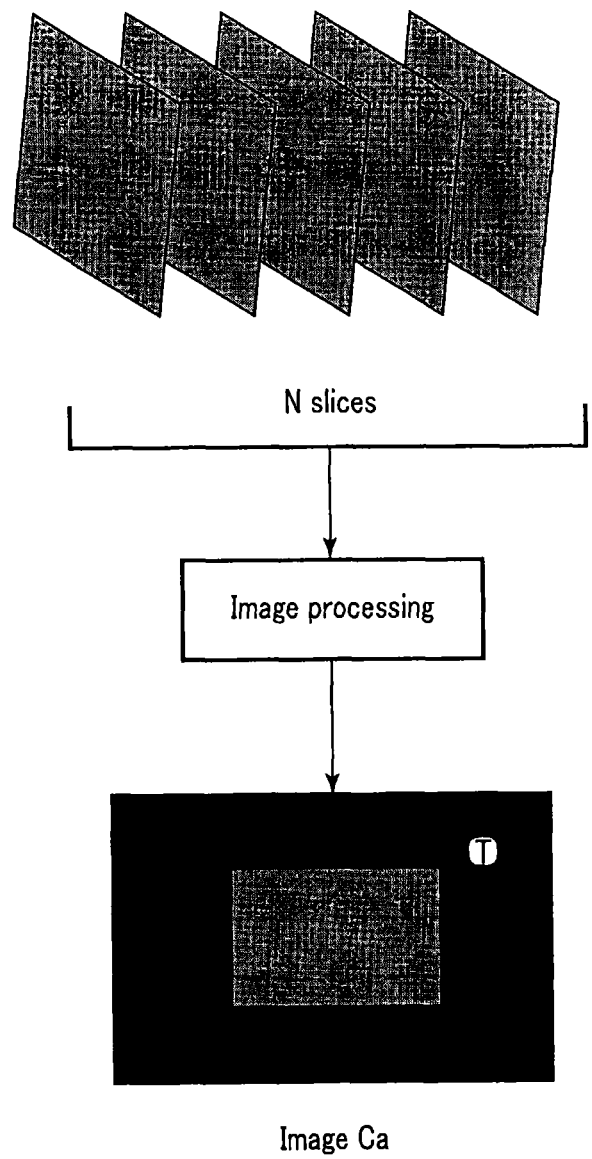
FIG. 7 is a view for explaining processing in step S4 according to the second modification.

When using a two-dimensional array probe as the ultrasound probe 12, the apparatus may perform processing in steps S3, S4, and S5 in the following manner. That is, as shown in FIG. 6, in processing in step S3, the apparatus acquires the puncture needle enhanced image group Bn by obliquely scanning n slices parallel to the slice direction, and executes averaging processing, addition/subtraction processing, or the like for luminance values at the respective spatially corresponding positions, thereby generating an image Ba. In addition, in processing in step S4, as shown in FIG. 7, the apparatus acquires a living body tissue image group Cn by normal scanning of n slices parallel to the slice direction, and executes averaging processing, addition/subtraction processing, or the like for luminance values at the respective spatially corresponding positions, thereby generating an image Ca. The apparatus may generate the puncture needle extraction image D by performing luminance value comparison processing or the like described above in step S5 using the images Ba and Ca obtained in this manner.

In addition, it is possible to visually check how the puncture needle has shifted from the position immediately below the ultrasound probe 12, by adjusting weights in averaging, addition processing, or the like in accordance with the distance of each image from the position immediately below the ultrasound probe 12, when generating the image Ba. Assume that the puncture needle is apart from the position immediately below the ultrasound probe 12 as the weights are decreased with an increase in distance from the position immediately below the ultrasound probe 12. In this case, the apparatus displays the low-luminance (dark) puncture needle in the paracentesis support image E. In contrast, if the puncture needle exists at the position immediately below the ultrasound probe 12, the apparatus displays the high-luminance (bright) puncture needle in the paracentesis support image E. The operator can easily grasp the positional relationship between the ultrasound probe 12 (and a scan region) and the puncture needle with reference to the luminance of the puncture needle displayed in the paracentesis support image E.

(Third Modification)

Figure 8:
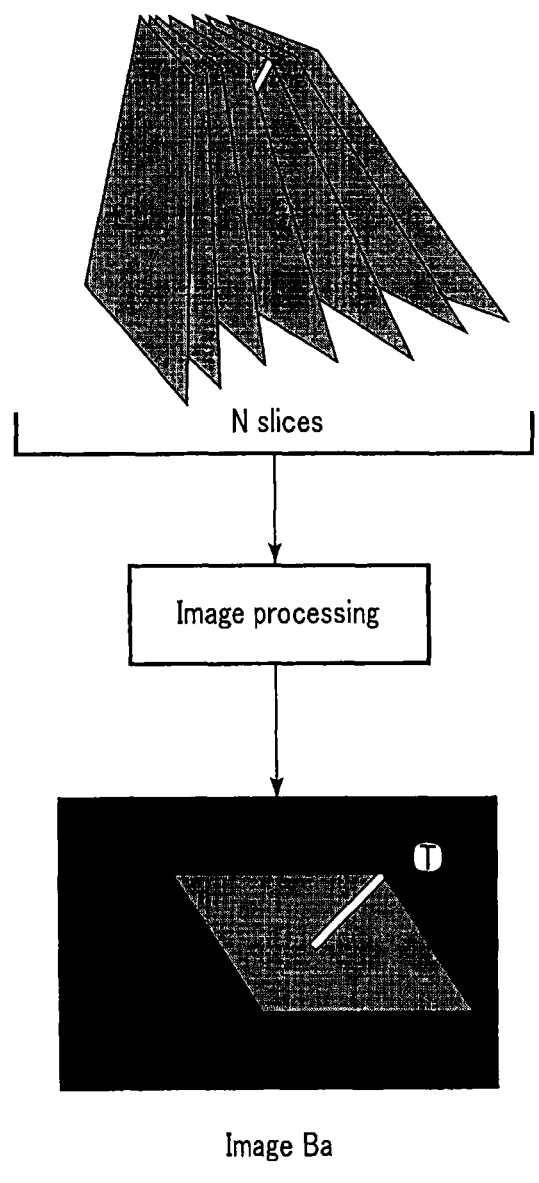
FIG. 8 is a view for explaining processing in step S3 according to the third modification.
Figure 9:
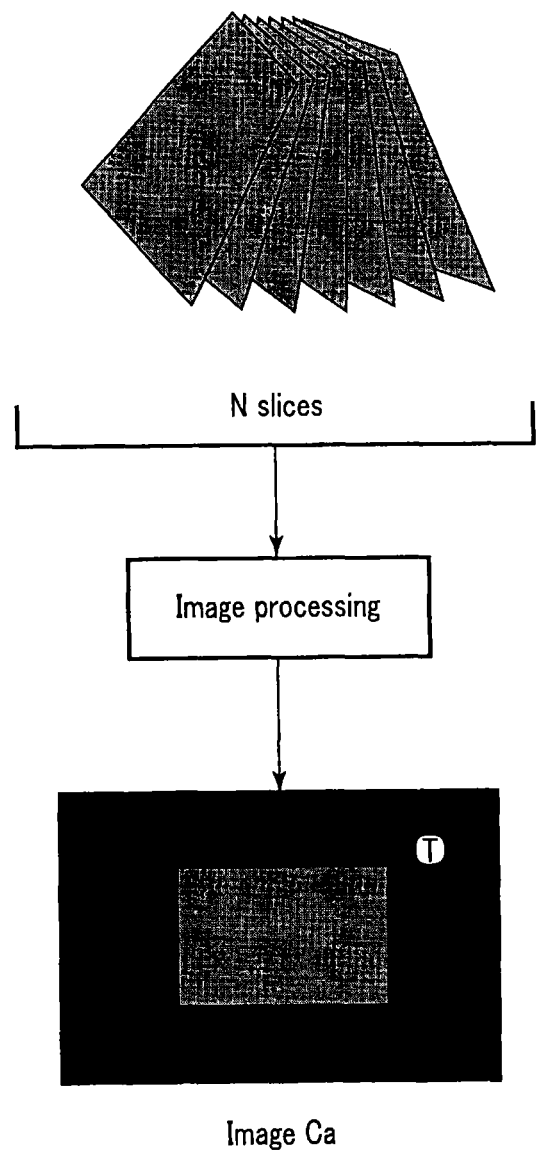
FIG. 9 is a view for explaining processing in step S4 according to the fourth modification.

When using a four-dimensional probe (a probe capable of scanning a three-dimensional region with time by swinging a one-dimensional transducer array) as the ultrasound probe 12, the apparatus may perform the processing in steps S3, S4, and S5 in the following manner as in the second modification. That is, in the processing in step S3, as shown in FIG. 8, the apparatus acquires the puncture needle enhanced image group Bn corresponding to n scan slices by obliquely scanning scan slices along the slice direction while swinging and moving (swinging) the probe, and generates the image Ba by executing averaging, addition/subtraction processing, or the like for luminance values at the respective spatially corresponding positions. In addition, in the processing in step S4, as shown in FIG. 9, the apparatus acquires the living body tissue image group Cn corresponding to n scan slices by normally scanning scan slices along the slice direction while swinging and moving (swinging) the probe, and generates the image Ca by executing averaging, addition/subtraction processing, or the like for luminance values at the respective spatially corresponding positions. The apparatus may generate the puncture needle extraction image D by performing the above luminance value comparison processing or the like in step S5 by using the images Ba and Ca obtained in this manner. Obviously, it is possible to perform the same weighting processing as that in the second modification.

As shown in FIG. 10, when the operator performs a paracentesis while monitoring a living body tissue and a puncture needle, the above ultrasound diagnostic apparatus acquires a puncture needle enhanced image by oblique scanning using a scan region which is set so as not to come off the puncture needle, and acquires a living body tissue image by normal scanning, which differs in only transmission/reception direction from the puncture needle enhanced image, thereby generating a puncture needle extraction image by using the puncture needle enhanced image and the living body tissue image. Since the puncture needle enhanced image and the living body tissue image are acquired under substantially the same transmission/reception conditions except for the transmission/reception directions, it is possible to generate a puncture needle extraction image from which the living body tissue is favorably removed by using the two images. The apparatus generates and displays a paracentesis support image including the living body tissue visualized with a high resolution and the favorably extracted puncture needle by using the puncture needle extraction image obtained in this manner and the high-resolution biological image obtained by tissue harmonic imaging and the like. The operator can execute a paracentesis safely and reliably without depending on his/her senses by observing a paracentesis support image always favorably visualizing a puncture needle and a living body tissue.

Second Embodiment

An ultrasound diagnostic apparatus according to the second embodiment will be described next. An ultrasound diagnostic apparatus 1 according to this embodiment acquires a puncture needle enhanced image B (or a puncture needle enhanced image group Bn; the puncture needle enhanced image B will be exemplified) corresponding to each of a plurality of oblique angles, and selects the puncture needle enhanced image B corresponding to an optimal oblique angle optimal for the visualization of the puncture needle based on the angle of the puncture needle inserted into the object. The apparatus generates a puncture needle extraction image D by using the selected image.

Note that when paracentesis support processing according to this embodiment is compared with paracentesis support processing according to the first embodiment, processing in steps S3 and S5 in FIG. 2 differs from that in the second embodiment. The second embodiment will be described below mainly on steps S3 and S5.

Figure 11:
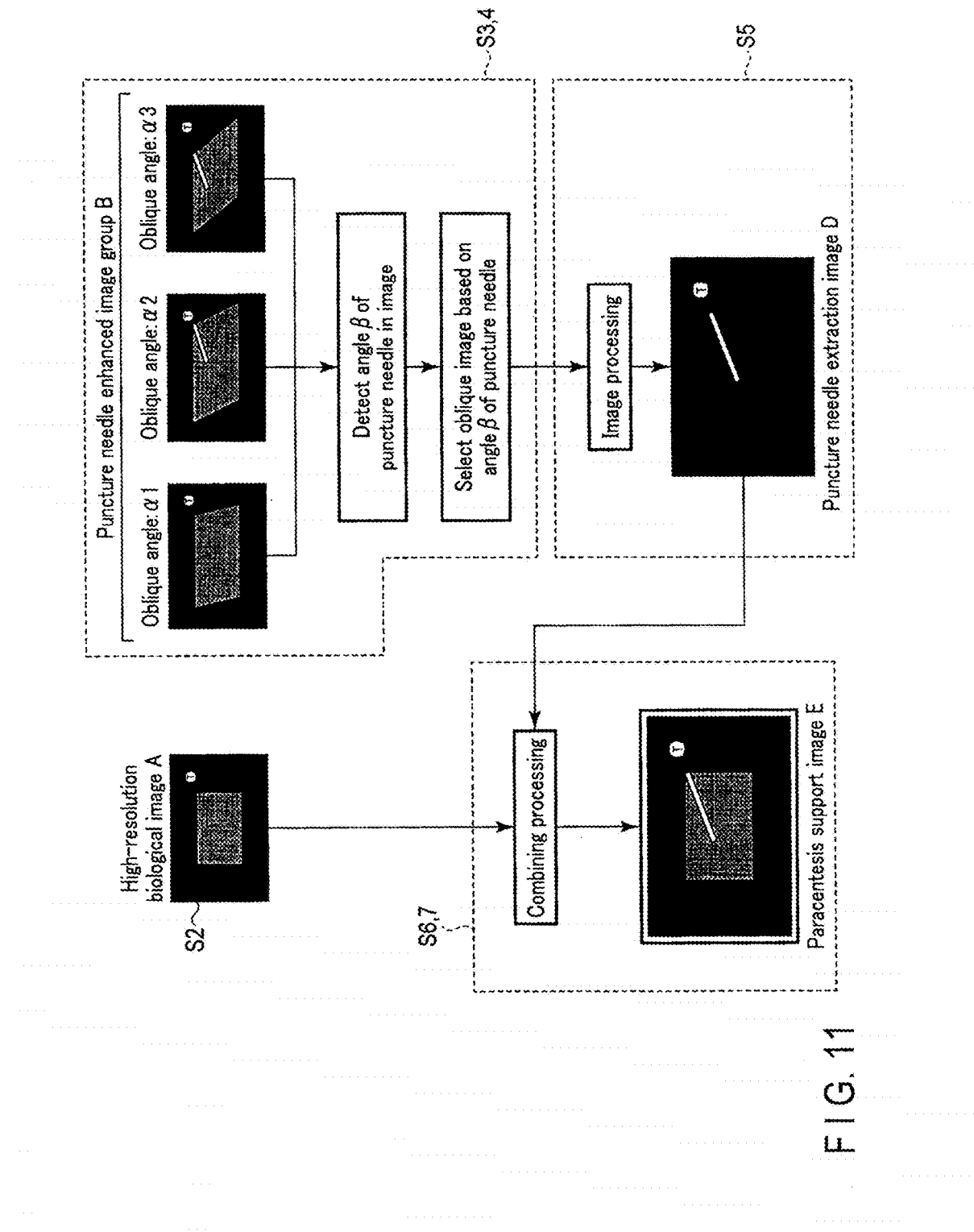
FIG. 11 is a view conceptually showing paracentesis support processing according to the second embodiment.

FIG. 11 is a view conceptually showing paracentesis support processing according to the second embodiment (the step numbers in FIG. 11 correspond to those shown in FIG. 2). As shown in FIG. 11, in step S3, the apparatus acquires the puncture needle enhanced image B corresponding to each of a plurality of oblique angles. It is possible to arbitrarily set a plurality of oblique angles. Assume that this embodiment uses three oblique angles, for example, $\alpha1=15°$, $\alpha2=30°$, and $\alpha3=45°$. Note that transmission/reception settings at the respective oblique angles are the same as those in the first embodiment.

In step S3 as well, a control processor 31 detects a puncture angle $\beta$ of the puncture needle relative to the object. It is possible to implement the detection of the puncture angle $\beta$ of the puncture needle by performing line segment detection processing by, for example, using at least one of the plurality of puncture needle enhanced images B. The apparatus may also detect a puncture angle by using, for example, a detector provided for a puncture needle adapter. In addition, the control processor 31 selects the puncture needle enhanced image B used for the generation of the puncture needle extraction image D from the plurality of puncture needle enhanced images B corresponding to a plurality of oblique angles based on the detected puncture angle $\beta$ of the puncture needle.

In step S5, a paracentesis support image generation unit 32 generates the puncture needle extraction image D by image processing using the selected puncture needle enhanced image B and a living body tissue image C. The specific contents of the image processing are the same as those in the first embodiment.

Note that the apparatus sequentially and repeatedly executes the processing in steps S2 to S7 (or the processing in steps S3 to S7) along with the progression of the paracentesis. For this reason, the control processor 31 preferably controls at least either a plurality of oblique angles or the number of oblique angles (the number of oblique directions) in accordance with the angle of the puncture needle and its temporal change detected in step S3. In this case, the apparatus decides and controls transmission/reception conditions in accordance with a plurality of decided oblique angles and the decided number of oblique angles.

(First Modification)

Figure 12:
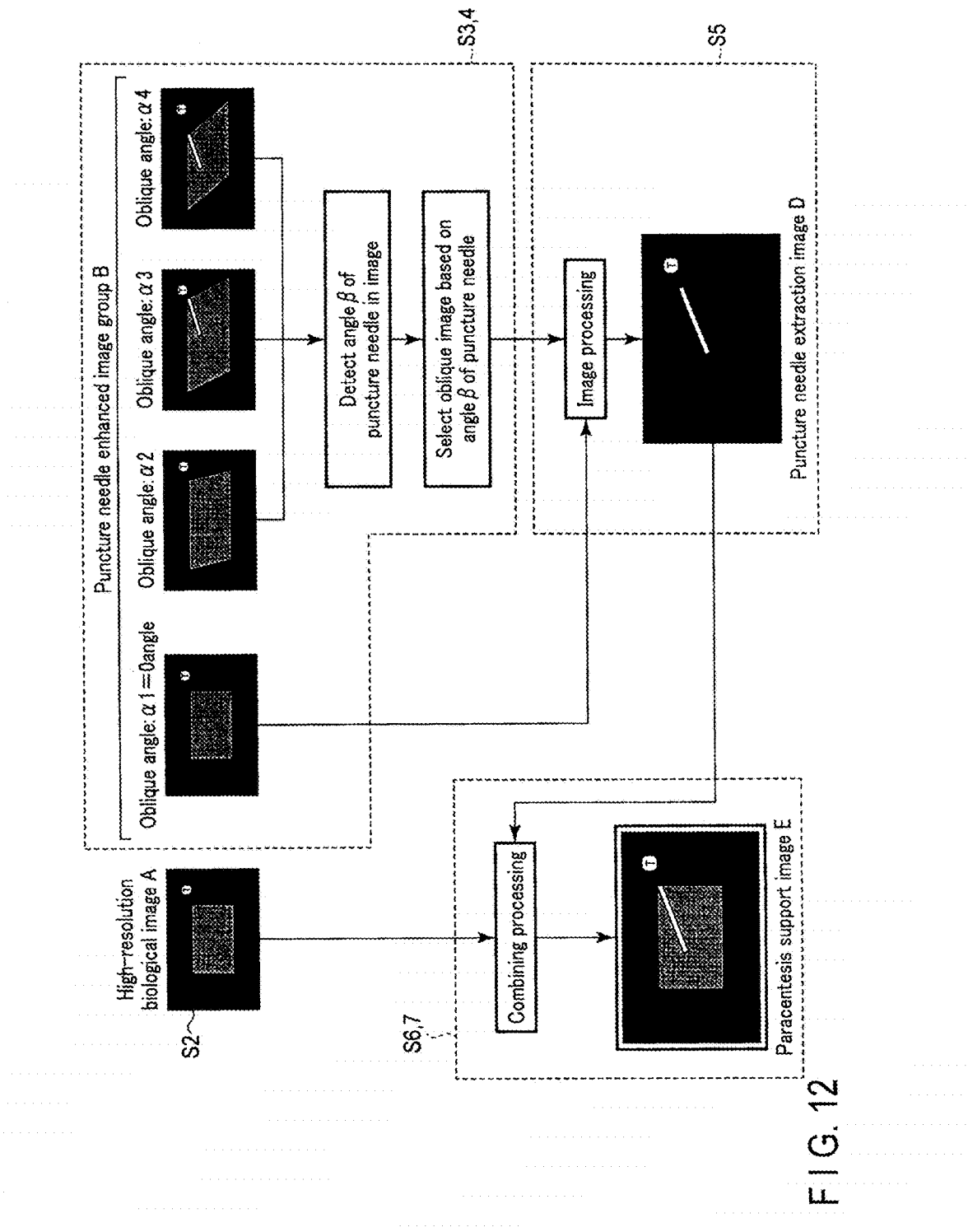
FIG. 12 is a view conceptually showing paracentesis support processing according to the first modification of the second embodiment.

In the above embodiment, for example, oblique angles are set as follows: $\alpha1=15°$, $\alpha2=30°$, and $\alpha3=45°$. In contrast to this, as shown in, for example, FIG. 12, the apparatus executes scanning in step S3 with oblique angle $\alpha0=0°$. The puncture needle enhanced image B obtained with oblique angle $\alpha0=0°$ is equivalent to the living body tissue image C acquired in the first embodiment. Therefore, it is possible to omit the acquisition processing for the living body tissue image C in step S4 by executing acquisition processing for the plurality of puncture needle enhanced images B including the image with oblique angle $\alpha0=0°$ in step S3.

(Second Modification)

Figure 13:
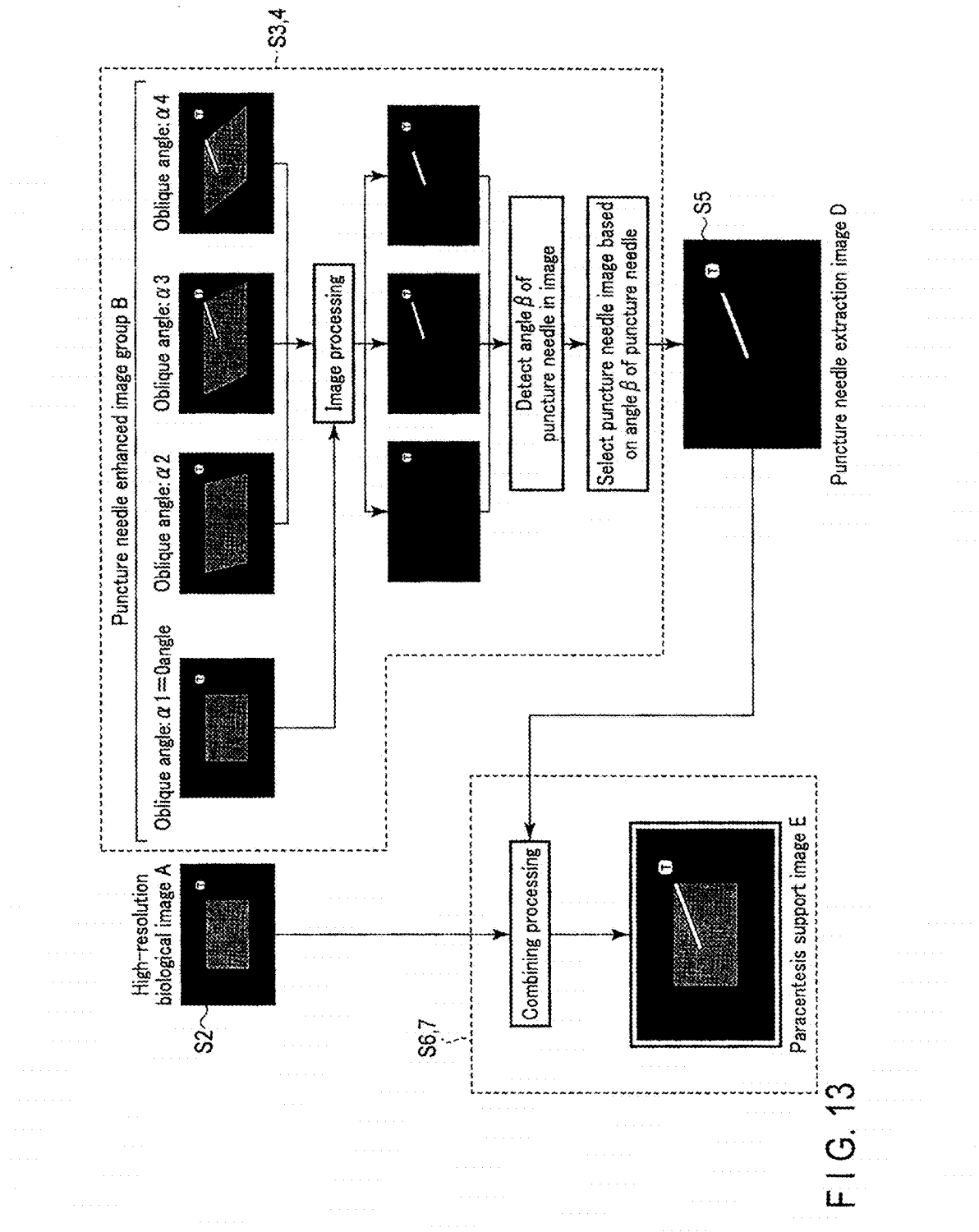
FIG. 13 is a view conceptually showing paracentesis support processing according to the second modification of the second embodiment.
Figure 14:
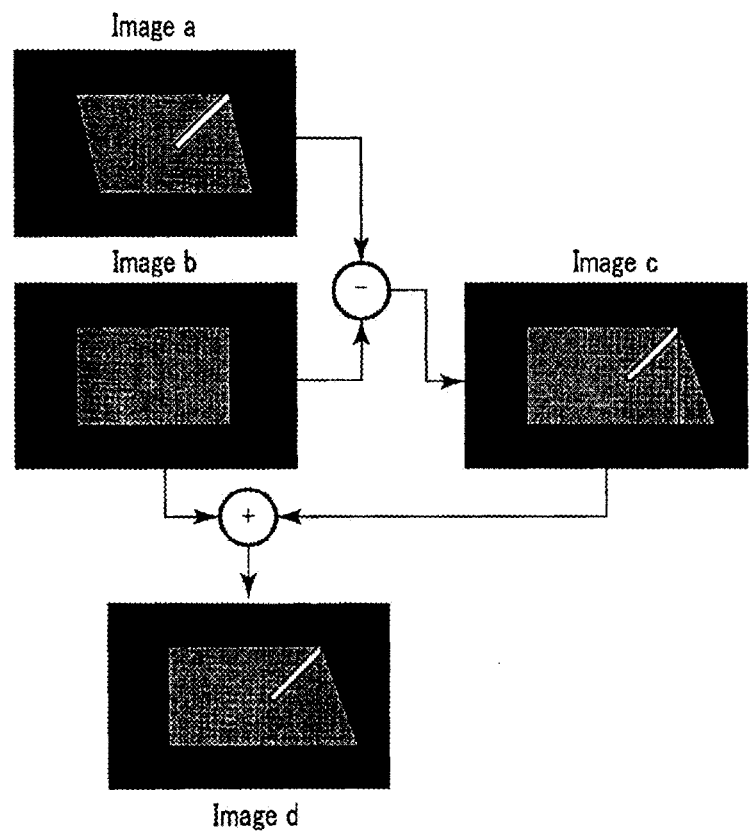
FIG. 14 is a view for explaining processing in a conventional ultrasound diagnostic apparatus.

Upon executing scanning with oblique angle $\alpha0=0°$ in step S3 as in the first modification of this embodiment, for example, as in FIG. 13, the apparatus may detect a puncture angle of the puncture needle and select the puncture needle enhanced image B used for the generation of the puncture needle extraction image D after performing image processing for the puncture needle enhanced image B corresponding to oblique angle $\alpha0=0°$ and the puncture needle enhanced images B corresponding to other oblique angles.

In general, the puncture angle of a puncture needle in an object differs for each surgical operation. The ultrasound diagnostic apparatus according to this embodiment acquires the puncture needle enhanced image B corresponding to each of a plurality of oblique angles, and selects the puncture needle enhanced image B corresponding to an oblique angle optimal for the visualization of the puncture needle based on the puncture angle of the puncture needle in the object. This apparatus can generate the puncture needle extraction image D and the paracentesis support image E by using the selected image. In a paracentesis, it is possible to always favorably visualize the puncture needle. This can contribute to an improvement in the safety and quality of a paracentesis.

Note that in the second embodiment and its modifications, the apparatus selects the puncture needle enhanced image B corresponding to an optimal oblique angle from a plurality of oblique images. However, the apparatus may use, for example, a maximum value projection image of a plurality of oblique images as the puncture needle enhanced image B. If the accuracy of puncture angle detection is low, since an optical puncture needle enhanced image may not be selected, it is possible to generate an image having an enhanced puncture needle image by performing maximum value projection without detection. The processing is not limited to a maximum value projection and may be averaging, addition, or the like.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

(1) The paracentesis support function according to each embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

(2) In each embodiment described above, the apparatus has executed paracentesis support processing by using luminance values after image reconstruction. In contrast to this, the apparatus may execute paracentesis support processing by using raw data before image reconstruction.

(3) Each embodiment described above has exemplified the case in which the puncture needle is prominently displayed in a paracentesis. However, it is also possible to actively visualize surgical or treatment instruments (e.g., a catheter, a bolt inserted into the object, and a foreign substance) other than the puncture needle by using the paracentesis support function according to each embodiment. That is, it is possible to visualize any target object which can amplify ultrasound reflection by executing scanning while actively controlling an oblique angle to set oblique transmission/reception direction, using the technique of this embodiment.

According to the present invention described above, it is possible to implement an ultrasound diagnostic apparatus which can monitor a living body tissue and a puncture needle with a favorable high-quality image when performing a paracentesis, and a method of controlling the ultrasound diagnostic apparatus.

The invention claimed is:

1. An ultrasound diagnostic apparatus which is used to observe a position and puncture direction of a puncture needle in an object in a paracentesis, comprising:
   an ultrasound probe configured to execute ultrasound scanning;
   data acquisition circuitry configured to acquire a first ultrasound data set by executing, using the ultrasound probe, a first ultrasound scan, under a first transmission/reception setting, concerning an inside of the object, acquire a plurality of second ultrasound data sets by executing, using the ultrasound probe, second ultrasound scans with different oblique angles, under a second transmission/reception setting, concerning the inside of the object, and acquire a third ultrasound data set by executing, using the ultrasound probe, a third ultrasound scan, under a third transmission/reception setting, concerning the inside of the object, wherein the first transmission/reception setting and the second transmission/reception setting are different in frequency setting, and the second transmission/reception setting and the third transmission/reception setting have a same frequency setting;
   image generation circuitry configured to generate a tissue image displaying a living body tissue by using the first ultrasound data set, generate a plurality of oblique images by using the plurality of second ultrasound data sets, generate a puncture-needle-enhanced image by using a maximum value projection process on the plurality of oblique images, generate a puncture image displaying the puncture needle based on the generated puncture-needle-enhanced image and an image generated by using the third ultrasound data set, and generate a composite image visualizing the living body tissue and the puncture needle by using the tissue image and the puncture image; and
   a display to display the composite image.

2. The ultrasound diagnostic apparatus according to claim 1, wherein the image generation circuitry is further configured to perform image processing, including one of comparison processing, addition processing, subtraction processing, and averaging processing for pixel values.

3. The ultrasound diagnostic apparatus according to claim 1, wherein an oblique angle differs in the second ultrasound scans and the third ultrasound scan, and the image generation circuitry is further configured to generate the puncture image based on a difference between the tissue image and the puncture needle-enhanced image.

4. The ultrasound diagnostic apparatus according to claim 1, wherein the first transmission/reception setting, the second transmission/reception setting, and the third transmission/reception setting include a transmission waveform, a transmission technique, a transmission frequency, a transmission/reception delay time, a reception center frequency, a reception frequency band, a transmission/reception angle relative to an electronic scanning direction, a transmission/reception angle in a slice direction, and a beam thickness in the slice direction.

5. The ultrasound diagnostic apparatus according to claim 1, wherein the data acquisition circuitry is further configured to execute the second ultrasound scans on a first region in the object, and execute the third ultrasound scan on a second region different from the first region in the object.

6. The ultrasound diagnostic apparatus according to claim 1, wherein the image generation circuitry is further configured to generate the tissue image by executing at least one of addition processing, subtraction processing, maximum value projection processing, minimum value projection processing, and averaging processing using the first ultrasound data set.

7. The ultrasound diagnostic apparatus according to claim 1, wherein the data acquisition circuitry is further configured to acquire the first ultrasound data set by executing the first ultrasound scan using a pulse subtraction method, and
   the image generation circuitry is further configured to generate the tissue image by executing addition processing or subtraction processing using the first ultrasound data set acquired by the pulse subtraction method.

8. The ultrasound diagnostic apparatus according to claim 1, wherein the data acquisition circuitry is further configured to acquire the plurality of second ultrasound data sets corresponding to the different oblique angles by executing a plurality of second transmissions/receptions with the different oblique angles, and
   the image generation circuitry is further configured to generate the puncture image by image processing using the plurality of second ultrasound data sets corresponding to any one of the different oblique angles, which is selected based on an angle of the puncture needle and the third ultrasound data set.

9. The ultrasound diagnostic apparatus according to claim 8, wherein the image processing includes one of comparison processing, maximum value holding processing, addition processing, subtraction processing, and averaging processing for pixel values.

10. The ultrasound diagnostic apparatus according to claim 8, wherein the data acquisition circuitry is further configured to acquire the plurality of second ultrasound data sets corresponding to the different oblique angles by executing the plurality of second transmissions/receptions including oblique angle=0°, and the image generation circuitry is further configured to execute the image processing for the second ultrasound data corresponding to the oblique angle=0° as the third ultrasound data set.

11. The ultrasound diagnostic apparatus according to claim 8, wherein the data acquisition circuitry is further configured to control at least either the different oblique angles or a number of the different oblique angles in accordance with the angle of the puncture needle.

12. A method of controlling an ultrasound diagnostic apparatus which is used to observe a position and puncture direction of a puncture needle in an object in a paracentesis, comprising:

acquiring a first ultrasound data set by executing, using an ultrasound probe, a first ultrasound scan, under a first transmission/reception setting, concerning an inside of the object;

acquiring a plurality of second ultrasound data sets by executing, using the ultrasound probe, second ultrasound scans with different oblique angles, under a second transmission/reception setting, concerning the inside of the object;

acquiring a third ultrasound data set by executing, using the ultrasound probe, a third ultrasound scan, under a third transmission/reception setting, concerning the inside of the object, wherein the first transmission/reception setting and the second transmission/reception setting are different in frequency setting, and the second transmission/reception setting and the third transmission/reception setting have a same frequency setting;

generating a tissue image displaying a living body tissue by using the first ultrasound data set;

generating a plurality of oblique images by using the plurality of second ultrasound data sets, generate a puncture-needle-enhanced image by using a maximum value projection process on the plurality of oblique images, generate a puncture image displaying the puncture needle using the generated puncture needle enhanced image and an image generated by using the third ultrasound data set;

generating a composite image visualizing the living body tissue and the puncture needle by using the tissue image and the puncture image; and displaying the composite image.

* * * * *